US00PP18858P2

(12) United States Plant Patent
Fischer-Tohl

(10) Patent No.: US PP18,858 P2
(45) Date of Patent: May 27, 2008

(54) ***GERANIUM* PLANT NAMED 'BALLURTANG'**

(50) Latin Name: *Pelargonium zonale*
Varietal Denomination: Ballurtang

(75) Inventor: Ilse Fischer-Tohl, Kirchlintein (DE)

(73) Assignee: Silze GmbH & Company KG, Weener (DE)

( * ) Notice: Subject to any disclaimer, the term of this patent is extended or adjusted under 35 U.S.C. 154(b) by 67 days.

(21) Appl. No.: 11/605,106

(22) Filed: Nov. 28, 2006

(51) Int. Cl.
*A01H 5/00* (2006.01)

(52) U.S. Cl. ..... Plt./325
(58) Field of Classification Search ..... Plt./325
See application file for complete search history.

*Primary Examiner*—Annette H Para
(74) *Attorney, Agent, or Firm*—Audrey Charles

(57) ABSTRACT

A new and distinct cultivar of *Geranium* plant named 'Ballurtang', characterized by its semi-double type medium orange-colored flowers, medium green-colored foliage with strong zonation, and vigorous, compact, and upright growth habit.

2 Drawing Sheets

Latin name of genus and species of plant claimed: *Pelargonium zonale.*
Variety denomination: 'Ballurtang'.

BACKGROUND OF THE INVENTION

The present invention relates to a new and distinct cultivar of *Geranium* plant botanically known as *Pelargonium zonale* and hereinafter referred to by the cultivar name 'Ballurtang'.

The new cultivar originated in a controlled breeding program in Weener, Germany during Summer 1999. The objective of the breeding program was the development of *Geranium* cultivars with unique flower coloration, medium green-colored foliage, and a vigorous, upright growth habit.

The new *Geranium* cultivar is the result of cross-pollination. The female (seed) parent of the new cultivar is SIL Aurora, not patented, characterized by its semi-double type medium orange-colored flowers, medium green-colored foliage with strong zonation, and very compact, bushy, and upright-mounded growth habit. The male (pollen) parent of the new cultivar is GEN Tamara 'Genor', not patented, characterized by its semi-double type dark red-colored flowers, medium green-colored foliage, and upright growth habit. The new cultivar was discovered and selected as a single flowering plant within the progeny of the above stated cross-pollination during May 2000 in a controlled environment at Weener, Germany.

Asexual reproduction of the new cultivar by terminal stem cuttings since May 2000 at Weener, Germany and West Chicago, Ill. has demonstrated that the new cultivar reproduces true to type with all of the characteristics, as herein described, firmly fixed and retained through successive generations of such asexual propagation.

SUMMARY OF THE INVENTION

The following characteristics of the new cultivar have been repeatedly observed and can be used to distinguish 'Ballurtang' as a new and distinct cultivar of *Geranium* plant:

1. Semi-double type medium orange-colored flowers;
2. Medium green-colored foliage with strong zonation; and
3. Vigorous, compact, and upright growth habit.

Plants of the new cultivar differ from plants of the female parent primarily in growth habit and from plants of the male parent primarily in flower color and growth habit.

Of the many commercially available *Geranium* cultivars known to the inventor, the most similar in comparison to the new cultivar is Allure™ Hot Coral 'BFP-1568', U.S. Plant Pat. No. 11,417. However, in side by side comparisons, plants of the new cultivar differ from plants of 'BFP-1568' in the following characteristics:

1. Plants of the new cultivar have a flower color different from plants of 'BFP-1568'; and
2. Plants of the new cultivar have a foliage and zone color different from plants of 'BFP-1568'.

BRIEF DESCRIPTION OF THE PHOTOGRAPHS

The accompanying photographs show, as nearly true as it is reasonably possible to make the same in color illustrations of this type, typical flower and foliage characteristics of the new cultivar. Colors in the photographs differ slightly from the color values cited in the detailed description, which accurately describes the colors of 'Ballurtang'. The plants were grown in 4.5 inch pots for 7 weeks in a greenhouse at West Chicago, Ill.

DETAILED BOTANICAL DESCRIPTION

Figure 1:
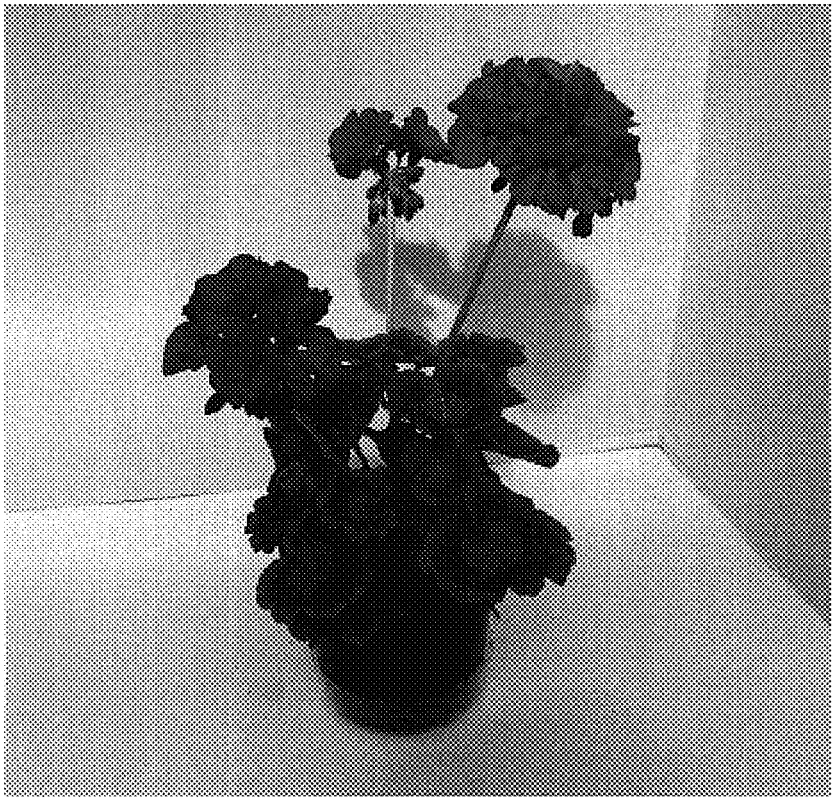
FIG. 1 illustrates a side view of the overall growth and flowering habit of 'Ballurtang'.
Figure 2:
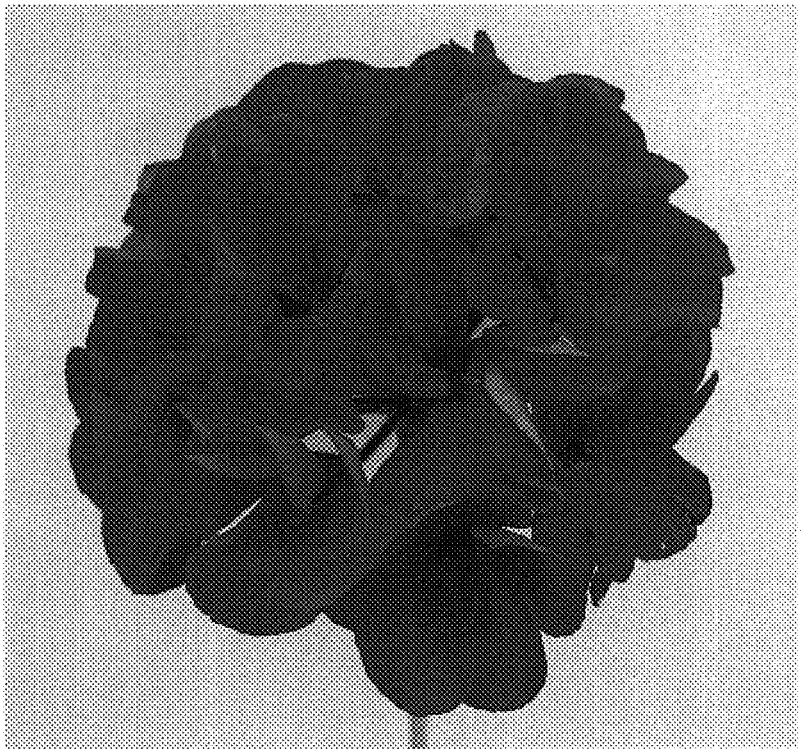
FIG. 2 illustrates a close-up view of an individual umbel of 'Ballurtang'.
Figure 3:
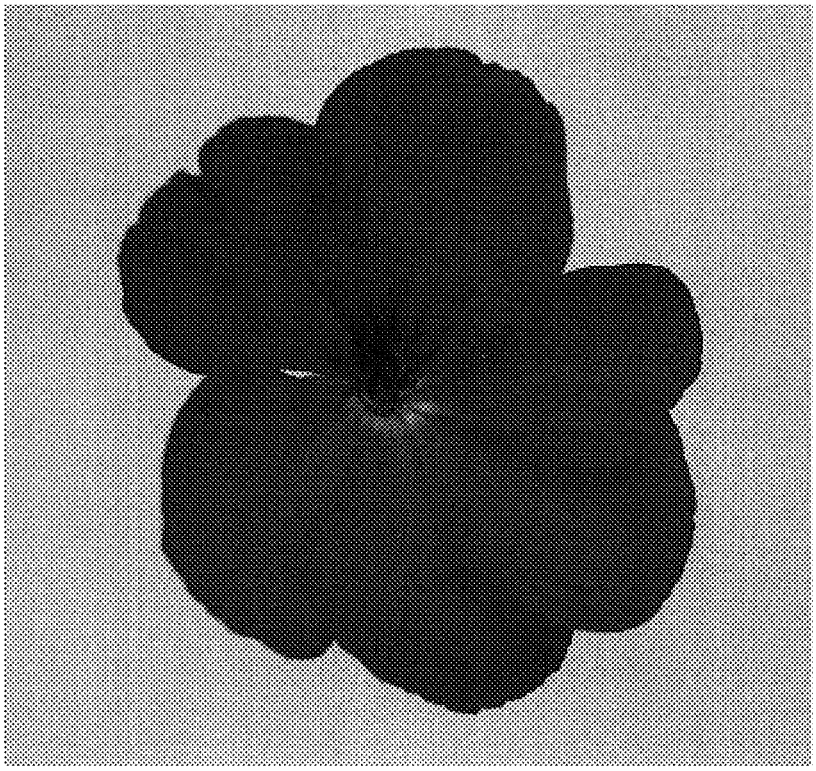
FIG. 3 illustrates a close-up view of an individual flower of 'Ballurtang'.
Figure 4:
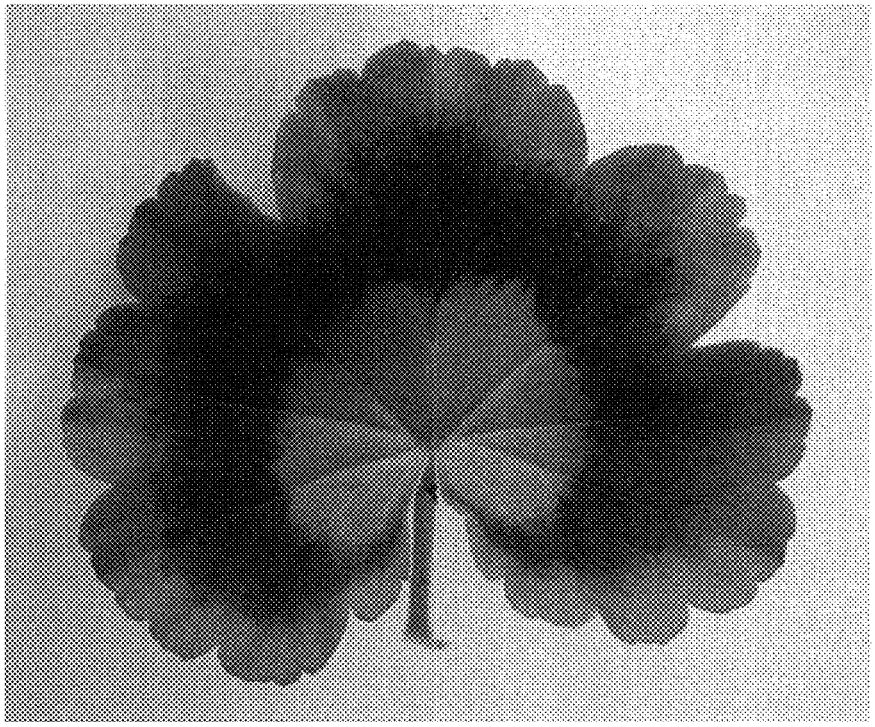
FIG. 4 illustrates a close-up view of an individual leaf of 'Ballurtang'.

The new cultivar has not been observed under all possible environmental conditions to date. Accordingly, it is possible that the phenotype may vary somewhat with variations in the environment, such as temperature, light intensity, and day length, without, however, any variance in genotype.

The chart used in the identification of colors described herein is The R.H.S. Colour Chart of The Royal Horticultural Society, London, England, 2001 edition, except where general color terms of ordinary significance are used. The color values were determined on Jul. 18, 2006 between 9:00 a.m. and 11:00 a.m. under natural light conditions in West Chicago, Ill.

The following descriptions and measurements describe plants produced from cuttings taken from stock plants and grown in a glass-covered greenhouse under conditions comparable to those used in commercial practice. The plants were grown at West Chicago, Ill. in 4.5 inch pots for 7 weeks utilizing a soilless growth medium. Greenhouse temperatures were maintained at approximately 70° F. to 77° F. (21° C. to 25° C.) during the day and approximately 65° F. to 68° F. (18° C. to 20° C.) during the night. Greenhouse light levels of 2,500 footcandles to 6,000 footcandles were maintained during the day.

Botanical classification: *Pelargonium zonale* cultivar Ballurtang.

Parentage:

*Female parent.*—SIL Aurora, not patented.

*Male parent.*—GEN Tamara 'Genor', not patented.

Propagation:

*Type cutting.*—Terminal stem.

*Time to initiate roots.*—Approximately 9 to 13 days.

*Time to produce a rooted cutting.*—Approximately 18 to 20 days.

*Root description.*—Fibrous.

*Rooting habit.*—Freely branching.

Plant description:

*Commercial crop time.*—Approximately 8 to 10 weeks from a rooted cutting.

*Growth habit and general appearance.*—Vigorous, upright.

*Size.*—Height from soil level to top of plant plane: Approximately 22.6 cm. Height from soil level to top of foliage: Approximately 11.4 cm. Width: Approximately 27.9 cm.

*Branching habit.*—Freely basal branching. Quantity of main branches per plant: Approximately 2.

*Branch.*—Strength: Strong. Length: Approximately 10.2 cm. Diameter: Approximately 6.5 mm. Length of central internode: Approximately 1.8 cm. Texture: Densely pubescent with a mixture of glandular and nonglandular hairs. Gland color: Mixture of 32B, transparent; and colorless, transparent. Color of young and mature stems: 144A.

Foliage description:

*General description.*—Quantity of leaves per lateral branch: Approximately 12. Fragrance: None. Form: Simple. Arrangement: Opposite.

*Leaves.*—Aspect: Petiole is at an acute angle to stem and blade is perpendicular to stem. Shape: Reniform. Margin: Crenate, palmately lobed. Apex: Obtuse. Base: Cordate. Venation pattern: Palmate. Length of mature leaf: Approximately 5.1 cm. Width of mature leaf: Approximately 8.6 cm. Texture of upper surface: Pubescent with a mixture of glandular and nonglandular hairs. Texture of lower surface: Pubescent with a mixture of glandular and non-glandular hairs, dense on venation. Gland color: Colorless, transparent. Color of upper surface of young foliage: Between 146B and 146A with venation of 144A. Color of lower surface of young foliage: 147B with venation of 146D. Color of upper surface of mature foliage: 137A with a strong zone of 178A and venation of 147D. Color of lower surface of mature foliage: 147B with venation of 147D.

*Petiole.*—Length: Approximately 5.4 cm. Diameter: Approximately 3.0 mm. Texture: Densely pubescent with a mixture of glandular and nonglandular hairs. Gland color: Mixture of 32C, transparent; and colorless, transparent. Color: 144A.

Flowering description:

*Flowering habit.*—'Ballurtang' is freely flowering under outdoor growing conditions with substantially continuous blooming from spring through autumn and year-round in greenhouse environment.

*Lastingness of individual flower on the plant.*—Approximately 13 to 15 days.

Inflorescence description:

*General description.*—Type: Umbel. Positioned above foliage. Quantity of fully open umbels per plant: Approximately 2. Quantity of developing umbels per plant: Approximately: 2. Fragrance: None. Length or height: Approximately 5.9 cm. Width: Approximately 10.6 cm. Quantity of fully open flowers per inflorescence: Approximately 20.

*Peduncle.*—Strength: Strong. Aspect: Erect. Length: Approximately 15.6 cm. Diameter: Approximately 3.8 mm. Texture: Glandular pubescent. Gland color: Colorless, transparent. Color: 144A.

Flower description:

*General description.*—Type: Semi-double.

*Bud.*—Rate of opening: Generally takes 4 to 6 days for bud to progress from first color to fully open flower.

*Bud just before opening.*—Shape: Elliptic. Length: Approximately 1.6 cm. Width: Approximately 7.1 mm. Sepal texture: Densely pubescent with a mixture of glandular and nonglandular hairs. Gland color: Mixture of 32B, transparent; and colorless, transparent. Petal texture: Glabrous. Petal color: N30A.

*Corolla.*—Shape: Round. Diameter: Approximately 4.7 cm. Depth: Approximately 2.1 cm.

*Petals/petaloids.*—Quantity: Approximately 6.1 petals and 2 irregularly-shaped petaloids per flower. Shape: Obovate. Appearance: Velvety, iridescent. Margin: Entire. Apex: Obtuse. Base: Attenuate. Length of upper petals: Approximately 2.8 cm. Width of upper petals: Approximately 1.9 cm. Length of lower petals: Approximately 2.6 cm. Width of lower petals: Approximately 2.2 cm. Texture of upper and lower surfaces: Glabrous. Color of upper surface of upper petals when fully open: N30B with margin of N30A and venation at base of 46A. Color of lower surface of upper petals when fully open: N30B with venation of 53B. Color of upper surface of lower petals when fully open: N30B with venation of 50A. Color of lower surface of lower petals when fully open: 40D with margin of N30B and faint venation at base of 40B.

*Calyx.*—Shape: 5-pointed star. Diameter: Approximately 2.1 cm.

*Sepals.*—Quantity per flower: Approximately 5. Shape: Lanceolate. Margin: Entire. Apex: Acuminate. Base: Fused. Length of upper sepal: Approximately 1.2 cm. Width of upper sepal: Approximately 4.0 mm. Length of lower sepals: Approximately 1.1 cm. Width of lower sepals: Approximately 3.0 mm. Texture of upper surface: Glabrous. Texture of lower surface: Densely pubescent with a mixture of glandular and nonglandular hairs. Gland color: Mixture of 32B, transparent; and colorless, transparent. Color of upper surface: 144A. Color of lower surface: 144A with and overlay 185A.

*Pedicel.*—Strength: Strong. Aspect: Acute angle to stem. Length: Approximately 3.0 cm. Diameter: Approximately 2.0 mm. Texture: Glandular pubescent. Gland color: 32B, transparent. Color: 144A with and overlay 185A.

*Reproductive organs.*—Androecium: Quantity of mature stamens: Approximately 7 per flower. Anther shape: Oblong. Anther length: Approximately 2.0 mm. Anther color: 70A. Pollen amount: Moderate. Pollen color: 31A. Gynoecium: Pistil quantity: 1 per flower. Pistil length: Approximately 9.0 mm. Stigma shape: 5 branched. Stigma length: Approximately 2.0 mm. Stigma color: 46C. Style length: Approximately 3.0 mm. Style color: 159B with an overlay of 70D. Ovary length: Approximately 4.0 mm. Ovary texture: Densely pubescent. Ovary color: 144A.

Seed and fruit production: Neither seed nor fruit production has been observed.

Disease and pest resistance: Resistance to pathogens and pests common to *Geranium* has not been observed.

What is claimed is:

1. A new and distinct cultivar of *Geranium* plant named 'Ballurtang', substantially as herein shown and described.

* * * * *